US009139837B2

(12) United States Patent
Serata et al.

(10) Patent No.: US 9,139,837 B2
(45) Date of Patent: Sep. 22, 2015

(54) HYDROGEN PEROXIDE RESISTANCE-IMPARTING GENE AND METHOD FOR USING SAME

(75) Inventors: Masaki Serata, Tama (JP); Mayumi Kiwaki, Kokubunji (JP); Tohru Iino, Kawasaki (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 94 days.

(21) Appl. No.: 14/003,094

(22) PCT Filed: Mar. 2, 2012

(86) PCT No.: PCT/JP2012/055401
§ 371 (c)(1),
(2), (4) Date: Sep. 4, 2013

(87) PCT Pub. No.: WO2012/121150
PCT Pub. Date: Sep. 13, 2012

(65) Prior Publication Data
US 2014/0141437 A1 May 22, 2014

(30) Foreign Application Priority Data

Mar. 4, 2011 (JP) ................. 2011-047841

(51) Int. Cl.
| | |
|---|---|
| *C12N 15/63* | (2006.01) |
| *C12N 15/74* | (2006.01) |
| *C07K 14/335* | (2006.01) |
| *C12Q 1/68* | (2006.01) |
| *A61K 35/747* | (2015.01) |
| *A61K 35/00* | (2006.01) |

(52) U.S. Cl.
CPC ............ *C12N 15/746* (2013.01); *A61K 35/747* (2013.01); *C07K 14/335* (2013.01); *C12Q 1/689* (2013.01); *A61K 2035/115* (2013.01)

(58) Field of Classification Search
None
See application file for complete search history.

(56) References Cited

U.S. PATENT DOCUMENTS

2012/0021418 A1 1/2012 Serata et al.

FOREIGN PATENT DOCUMENTS

| CN | 101139557 A | 3/2008 |
|---|---|---|
| CN | 101144062 A | 3/2008 |
| EP | 2 287 299 A1 | 2/2011 |
| JP | 2001 317292 | 11/2001 |
| WO | 2009 150856 | 12/2009 |

OTHER PUBLICATIONS

Zhang et al., Journal of Bacteriology, vol. 192 (2010) pp. 5268-5269.*

GenEmbl Sequence Search Result.*
"*Lactobacillus casei* BL23 complete genome, strain BL23", Database GenBank:FM177140.1, *Lactobacillus casei* BL23, Retrieved from the Internet: URL:http://www.ncbi.nlm.nih.gov/nuccore/fm177140, Total pp. 3, (May 9, 2010).
Serata, M. et al., "*Lactobacillus casei* YIT 9029 (Shirota-kabu) ni Okeru Sanso Kasanka Suiso Stress Oto no Kaiseki", Journal of Japan Society for Lactic Acid Bacteria, vol. 19 No. 2, p. 122, (Jun. 15, 2008) (with English translation).
Sako, T. et al., "Genetical and reverse-genetical analyses of functions from *Lactobacillus casei* strain Shirota in post-genomic era", Abstracts of the Annual Meeting of the Society for Biotechnology, vol. 58, p. 77, (Aug. 3, 2006) (with English translation).
Lee, J. et al., "Resistance of *Lactobacillus casei* KCTC 3260 to Reactive Oxygen Species (ROS): Role for a Metal Ion Chelating Effect", Journal of Food Science, vol. 70, No. 8, pp. M388 to M391, (2005).
Sato, T. et al., "Genome Analysis of Lactic Acid Bacteria and Bifidobacteria: Genome Analysis of *Lactobacillus casei* and *Bifidobacterium breve*", Journal of Intestinal Microbiology, vol. 18, pp. 135 to 140, (2004) (with English translation).
Rochat, T. et al., "Production of a Heterologous Nonheme Catalase by *Lactobacillus casei*: An Efficient Tool for Removal of H2O2 and Protection of *Lactobacillus bulgaricus* from Oxidative Stress in Milk", Applied and Environmental Microbiology, vol. 72, No. 8, pp. 5143 to 5149, (2006).
Serata, M. et al., "*Lactobacillus casei* Yit 9029 (Shirota-kabu) no Shinki Kasanka Suiso Taisei Idenshi no Kino Kaiseki", Japan Society fro Bioscience, Biotechnology, and Agrochemistry 2011 Nendo Taikai Koen Yoshishu, p. 108, (Mar. 5, 2011).
Serrano, L. Mariela et al., "Thioredoxin reductase is a key factor in the oxidative stress response of *Lactobacillus plantarum* WCFSI", Microbial Cell Factories, BioMed Central, p. 1 to 14, (Aug. 28, 2007).
Rocha, E. R. et al., "Thioredoxin Reductase Is Essential for Thiol/Disulfide Redox Control and Oxidative Stress Survival of the Anaerobe *Bacteroides fragilis*", Journal of Bateriology, vol. 189, No. 22, pp. 8015 to 8023, (Nov. 2007).
Vido, K. et al., "Roles of Thioredoxin Reductase during the Aerobic Life of *Lactococcus lactis*", Journal of Bacteriology, vol. 187, No. 2, pp. 601 to 610, (Jan. 2005).

(Continued)

*Primary Examiner* — Jim Ketter
(74) *Attorney, Agent, or Firm* — Oblon, McClelland, Maier & Neustadt, L.L.P.

(57) ABSTRACT

Provided is a gene that is useful for imparting hydrogen peroxide resistance to a microorganism. Also provided is a method for using the same. The hydrogen peroxide resistance-imparting gene encoding a protein selected from the following proteins (a) to (c): (a) a protein having the amino acid sequence of SEQ ID NO: 2; (b) a protein which has an amino acid sequence equivalent to the amino acid sequence of (a), except that one to several amino acid residues are deleted, substituted, or added, and which exhibits hydrogen peroxide resistance-imparting activity; and (c) a protein which has an amino acid sequence having an identity of 85% or higher to the amino acid sequence of (a), and which exhibits hydrogen peroxide resistance-imparting activity.

6 Claims, 3 Drawing Sheets

(56) References Cited

OTHER PUBLICATIONS

Written Opinion of the International Searching Authority Issued Mar. 27, 2012 in PCT/JP12/055401 Filed Mar. 2, 2012.

International Search Report Issued Mar. 27, 2012 in PCT/JP12/55401 Filed Mar. 2, 2012.

Combined Chinese Office Action and Search Report issued Aug. 28, 2014 in Patent Application No. 201280011277.3 with English Translation and English Translation of Category of Cited Documents.

Maze, A., et al., "Complete Genome Sequence of the Probiotic *Lactobacillus casei* strain BL23", J. Bacteriol. 192 (10), www.ncbi.nlm.nih.gov, May 9, 2010, 1 page.

Extended European Search Report issued Aug. 4, 2014 in European Patent Application No. 12755465.7.

Database UniProt [Online], Sep. 2, 2008, "SubName: Full=Putative uncharacterized protein;", XP002727339, retrieved from EBI accession No. UNIPROT:B3WBI8, Database accession No. B3WBI8, Database entry from Nov. 30, 2010; sequence-& A. Maze, et al., "Complete Genome Sequence of the Probiotic *Lactobacillus casei* Strain BL23", Journal of Bacteriology, vol. 192, No. 10, XP55129259, (May 15, 2010), pp. 2647-2648.

Database UniProt [Online], Nov. 14, 2006, "SubName: Full=Uncharacterized protein;", XP002727340, retrieved from EBI accession No. UNIPROT:Q033V7, Database accession No. Q033V7, Database entry from Nov. 30, 2010; sequence-& K. Makarova, et al., "Comparative genomics of the lactic acid bacteria", Proceedings of the National Academy of Sciences, vol. 103, No. 42, XP055004004, (Oct. 17, 2006), pp. 15611-15616.

Database UniProt [Online], Jun. 16, 2009, "SubName: Full=Uncharacterized protein;", XP002727341, retrieved from EBI accession No. UNIPROT:C2F914, Database accession No. C2F914, Database entry from Nov. 2, 2010; sequence.

Haoran AN, et al., "High-Level Expression of Heme-Dependent Catalase Gene katA from *Lactobacillus sakei* Protects *Lactobacillus rhamnosus* from Oxidative Stress", Molecular Biotechnology, vol. 45, No. 2, XP55129503, (Mar. 3, 2010-Jun. 1, 2010), pp. 155-160.

Willem M. DeVos, et al., "Metabolic engineering of sugar catabolism in lactic acid bacteria", Antonie Van Leeuwenhoek, vol. 70, No. 2/O4, XP000866282, (Oct. 1, 1996), pp. 223-242.

* cited by examiner

M: marker
CL: cell lysate
FT: Flow through
W: wash
E1 and E2: elution

HYDROGEN PEROXIDE RESISTANCE-IMPARTING GENE AND METHOD FOR USING SAME

TECHNICAL FIELD

The present invention relates to a gene which imparts hydrogen peroxide resistance to a microorganism, and a method for using the gene.

BACKGROUND ART

Many aerobic microorganisms have a respiratory chain responsible for oxygen metabolism and can acquire energy in the presence of oxygen, and can be grown well in the presence of oxygen. Such aerobic microorganisms also have a mechanism of detoxifying superoxide anion or hydrogen peroxide, which may be generated from a portion of oxygen through metabolism thereof, with the aid of, for example, superoxide dismutase, catalase, or peroxidase, which enzyme eliminates the toxicity of such reactive oxygen species.

Lactic acid bacteria, which are known to be useful among anaerobic microorganisms, are facultative anaerobes, and are considered to have neither a respiratory chain nor catalase. However, many lactic acid bacteria can be grown even in the presence of oxygen and exhibit oxygen resistance. Hitherto, some studies have been conducted on the oxygen resistance mechanism of lactic acid bacteria and have shown that lactic acid bacteria have, for example, NADH oxidase or pyruvate oxidase as an oxygen-metabolizing enzyme. As has been reported, NADH oxidase is classified into two types, that is, water-forming type and hydrogen peroxide-forming type, and water-forming type NADH oxidase detoxifies oxygen by four-electron reduction to form water, whereas hydrogen peroxide-forming type NADH oxidase generates hydrogen peroxide by two-electron reduction. As has also been reported, in a lactic acid bacterium such as *Streptococcus mutans*, alkyl hydroperoxide reductase converts hydrogen peroxide into water, and these enzymes function as a two-component peroxidase.

In addition, some lactic acid bacteria have been reported to have, for example, superoxide dismutase, catalase, or NADH peroxidase, which eliminates superoxide anion or hydrogen peroxide generated from oxygen.

Studies have suggested that *Lactobacillus plantarum* WCFS1 exhibits enhanced resistance to oxidative stress such as hydrogen peroxide by enhancing expression of the thioredoxin reductase gene, and thus thioredoxin reductase plays an important role in resistance to oxidative stress (Non-Patent Document 1).

In *Bacteroides fragilis*, which is an anaerobic Gram-negative bacterium, only a thioredoxin-thioredoxin reductase system is considered to be responsible for redox reaction of thiol/disulfide. It has been reported that when thioredoxin reductase is deleted, the bacterium cannot be grown even under anaerobic conditions without addition of a reducing agent such as cysteine and dithiothreitol (Non-Patent Document 2).

In addition, as has been reported, *Escherichia coli* includes therein a glutathione-glutathione reductase system or a thioredoxin-thioredoxinreductase system, which is essential for maintaining the intracellular environment in a reduced state, and gene-disrupted strains involved in such a system are sensitive to oxidative stress including hydrogen peroxide.

As has been reported, growth of *Lactococcus lactis* is inhibited under aerobic conditions through disruption of thioredoxin reductase (Non-Patent Document 3). However, relation between growth inhibition of the bacterium and oxygen resistance thereof has not been elucidated, since growth of the bacterium under aerobic conditions is restored by addition of dithiothreitol, and the amount of cells of the bacterium after 24-hour culturing is nearly equal to that of wild type cells of the bacterium.

As has also been reported, a mutant strain of *Streptococcus mutans* obtained through knockout of both NADH oxidase and alkyl hydroperoxide reductase (ahpC) exhibits oxygen resistance, and thus the gene for another iron-binding protein is responsible for oxygen resistance (Patent Document 1). However, such a gene is not necessarily present in all microorganisms, and the mechanism of oxygen resistance has not yet been fully elucidated. As described above, a plurality of genes are related with oxygen resistance; that is, it is not the case that only a single gene is responsible for imparting oxygen resistance to a microorganism. Therefore, difficulty is encountered in practically using it.

It has been also reported by the inventors of the present invention that fnr gene present in *Lactobacillus casei* and *Lactobacillus rhamnosus* is a particularly required gene for bacterial growth under an aerobic condition, and it is also an oxygen resistance-imparting gene (Patent Document 2).

However, regarding an oxidative stress, resistance to hydrogen peroxide generated during metabolism is also important. In this regard, although there has been a report about a gene involved with elimination of hydrogen peroxide such as NADH peroxidase or catalase in microorganisms of genus *Lactobacillus*, a gene directly exhibiting hydrogen peroxide resistance has not yet been identified.

CITATION LIST

Patent Document

Patent Document 1: JP-A-2001-327292
Patent Document 2: WO 2009/150856

Non-Patent Document

Non-Patent Document 1: L. Mariela Serrano et al. Microbial Cell Factories 6: 29 (2007)
Non-Patent Document 2: Edson R. Rocha et al. J. Bacteriol. 189: 8015-8023 (2007)
Non-Patent Document 3: Karin Vido et al. J. Bacteriol. 187: 601-610 (2005)

SUMMARY OF THE INVENTION

Problems to be Solved by the Invention

The present invention relates to provision of a gene which imparts hydrogen peroxide resistance to a microorganism as well as a method for using the gene.

Means for Solving the Problems

The present inventors have conducted studies on the genomic information of *Lactobacillus casei* YIT 9029 (FERM BP-1366), and as a result have found that there is a gene capable of suppressing production of hydroxyl radicals even under exposure to hydrogen peroxide, and by using the gene, hydrogen peroxide resistance can be imparted to a microorganism or the hydrogen peroxide resistance intrinsic to the microorganism can be enhanced.

Accordingly, the present invention relates to the followings.

1) A hydrogen peroxide resistance-imparting gene encoding a protein selected from the following proteins (a) to (c):
   (a) a protein having the amino acid sequence of SEQ ID NO: 2;
   (b) a protein which has an amino acid sequence equivalent to the amino acid sequence of (a), except that one to several amino acid residues are deleted, substituted, or added, and which exhibits hydrogen peroxide resistance-imparting activity; and
   (c) a protein which has an amino acid sequence having an identity of 85% or higher to the amino acid sequence of (a), and which exhibits hydrogen peroxide resistance-imparting activity.

2) A hydrogen peroxide resistance-imparting gene having a polynucleotide selected from the following polynucleotides (d) to (f):
   (d) a polynucleotide having the nucleotide sequence of SEQ ID NO: 1;
   (e) a polynucleotide which hybridizes, under stringent conditions, with a polynucleotide having a nucleotide sequence complementary to the nucleotide sequence of (d), and which encodes a protein exhibiting hydrogen peroxide resistance-imparting activity; and
   (f) a polynucleotide which has a nucleotide sequence having an identity of 85% or higher to the nucleotide sequence of (d), and which encodes a protein exhibiting hydrogen peroxide resistance-imparting activity.

3) A method for imparting hydrogen peroxide resistance to or enhancing hydrogen peroxide resistance in a microorganism, comprising introducing any of the aforementioned genes into the microorganism, or modifying the gene present in the microorganism.

4) A microorganism into which any of the aforementioned genes has been introduced or in which the gene has been modified.

5) A food or beverage containing the aforementioned microorganism.

6) A pharmaceutical product containing the aforementioned microorganism.

7) A screening method for selecting a microorganism exhibiting hydrogen peroxide resistance, comprising determining the presence or absence of any of the aforementioned genes, and/or determining the level of expression of the gene.

8) A recombinant vector containing any of the aforementioned polynucleotides or a portion thereof.

9) A host microorganism containing the aforementioned recombinant vector.

10) A nucleic acid fragment which specifically hybridizes with any of the aforementioned polynucleotides.

11) A DNA array or DNA chip containing any of the aforementioned polynucleotides or a portion thereof.

Effects of the Invention

Employment of the gene or polynucleotide of the present invention can impart hydrogen peroxide resistance to a microorganism or enhance hydrogen peroxide resistance of a microorganism, or enables selection, through screening, of a microorganism exhibiting hydrogen peroxide resistance. In the microorganism given with hydrogen peroxide resistance or enhanced hydrogen peroxide resistance, production of hydroxyl radicals is suppressed even under exposure to hydrogen peroxide, and thus problems occurring in cell constituting components such as nucleic acids, proteins, and lipids are suppressed.

Employment of a microorganism into which the gene of the present invention has been introduced or in which the gene has been modified realizes production of a food, beverage, or pharmaceutical product exhibiting resistance to oxidative stresses of interest. Since the number of living cells of the microorganism can be maintained at a high level even in the presence of oxygen, production of such a product does not require an anaerobic apparatus or an anaerobic storage container, and thus the product can be produced at low cost. In general, the greater the number of living cells of a microorganism, the higher the physiological effects of the microorganism. Thus, the present invention enables a microorganism to effectively exhibit its physiological effects.

MODES FOR CARRYING OUT THE INVENTION

Figure 1:
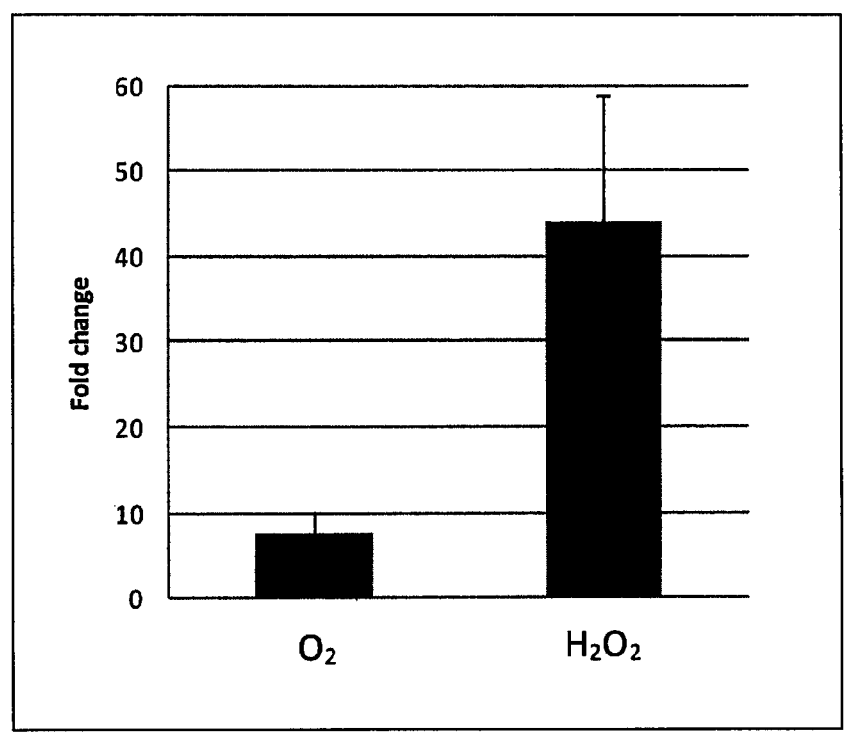
FIG. 1 is a graph illustrating a change of CDS2657 gene expression caused by oxidative stress.

In the present invention, identity (homology) between amino acid sequences and that between nucleotide sequences can be determined through the Lipman-Pearson method (Lipman, D. J. and Pearson, W. R. 1985. Rapid and sensitive protein similarity searches. Science 227: 1435-1441) by use of genetic information processing software GENETYX (manufactured by Genetyx Corporation) employing a homology analysis (search homology) program. Specifically, homology is calculated through, for example, analysis of data on comparison between a known gene and a gene of *Lactobacillus casei* YIT 9029 (parameters are as follows: unit size to compare=2, pick up location=5), and the results are exhibited in % scale.

As used herein, the term "gene" refers to a double-stranded DNA fragment, as well as a single-stranded DNA such as a sense strand or antisense strand fragment which forms such a double-stranded DNA. No particular limitation is imposed on the length of such a DNA. Examples of the polynucleotide include RNA and DNA, and examples of DNA include cDNA, genomic DNA, and synthetic DNA.

The hydrogen peroxide resistance-imparting gene of the present invention is a CDS2657 gene found in *Lactobacillus casei* YIT 9029 and also a gene deduced from the CDS2657 gene, and it encodes a protein exhibiting hydrogen peroxide resistance-imparting activity.

The CDS2657 gene is a so-called gene with unknown function, that is, function of the protein encoded by the gene is not identified (that is, hypothetical protein).

Specifically, the hydrogen peroxide resistance-imparting gene according to the present invention is a gene encoding a protein selected from the following proteins (a) to (c):
   (a) a protein having the amino acid sequence of SEQ ID NO: 2;
   (b) a protein which has an amino acid sequence equivalent to the amino acid sequence of (a), except that one to several amino acid residues are deleted, substituted, or added, and which exhibits hydrogen peroxide resistance-imparting activity; and (c) a protein which has an amino acid sequence having an identity of 85% or higher to the amino acid sequence of (a), and which exhibits hydrogen peroxide resistance-imparting activity.

The protein having the amino acid sequence of SEQ ID NO: 2 is a protein derived from *Lactobacillus casei* YIT 9029.

The amino acid sequence of SEQ ID NO: 2 in which one or more amino acid residues are deleted, substituted, or added encompasses an amino acid sequence obtained through deletion, substitution, or addition of one to several amino acid residues, and preferably 1 to 10 amino acid residues. As used herein, "addition" encompasses addition of one to several amino acid residues to both ends of an amino acid sequence.

The deletion, substitution, or addition of an amino acid residue (s) encompasses those which may be yielded by a naturally occurring mutation such as single-nucleotide substitution or by mutation artificially introduced to a gene according to site-directed mutagenesis or mutagenic treatment in a protein having the amino acid sequence of SEQ ID NO: 2, for example. In the case of artificial deletion, substitution, or addition of an amino acid residue(s), for example, a polynucleotide having a nucleotide sequence encoding the amino acid sequence of SEQ ID NO: 2 is subjected to a conventional site-directed mutagenesis, followed by expression of the polynucleotide through a customary method.

Amino acid residue substitution may be, for example, a substitution by an amino acid residue which exhibits characteristics such as hydrophobicity, electric charge, pK, and conformational feature that are similar to those of the original amino acid residue.

The amino acid sequence having an identity of 85% or higher to the amino acid sequence of (a) refers to an amino acid sequence which, upon appropriate alignment, exhibits an identity of 85% or higher, preferably 90% or higher, and more preferably 95% or higher to the amino acid sequence of SEQ ID NO: 2.

As used herein, the expression "impart hydrogen peroxide resistance" refers to the case in which sensitivity of a microorganism to hydrogen peroxide is lowered; specifically, a microorganism is rendered capable of growing even in the presence of oxygen, and/or a grown microorganism is not killed even in the presence of oxygen. Specifically, even when the microorganism is exposed to hydrogen peroxide either internally or externally, production of hydroxyl radicals is suppressed, and thus problems occurring in cell constituting components such as nucleic acids, proteins, and lipids as caused by the hydroxyl radicals are suppressed.

The hydrogen peroxide resistance-imparting gene of the present invention is preferably a gene having a polynucleotide selected from the following polynucleotides (d) to (f):

(d) a polynucleotide having the nucleotide sequence of SEQ ID NO: 1;

(e) a polynucleotide which hybridizes, under stringent conditions, with a polynucleotide having a nucleotide sequence complementary to the nucleotide sequence of (d), and which encodes a protein exhibiting hydrogen peroxide resistance-imparting activity; and (f) a polynucleotide which has a nucleotide sequence having an identity of 85% or higher to the nucleotide sequence of (d), and which encodes a protein exhibiting hydrogen peroxide resistance-imparting activity.

Herein, polynucleotide having the nucleotide sequence of SEQ ID NO: 1 is a DNA (CDS2657 gene) derived from *Lactobacillus casei* YIT 9029, and it imparts hydrogen peroxide resistance to a microorganism, and enables the microorganism to grow in the presence of hydrogen peroxide.

As used herein, the expression "under stringent conditions" refers to, for example, the case in which hybridization is carried out under conditions described in Molecular Cloning—a Laboratory manual 2nd edition (Sambrook, et al., 1989); specifically, the case in which hybridization is carried out in a solution containing 6×SSC (composition of 1×SSC: 0.15 M sodium chloride, 0.015 M sodium citrate, pH 7.0), 0.5% SDS, 5×Denhardt's solution, and 100 mg/mL herring sperm DNA together with a polynucleotide having a nucleotide sequence complementary to any of the aforementioned nucleotide sequences constantly keeping at 65° C. for 8 to 16 hours.

The expression "nucleotide sequence having an identity of 85% or higher to the nucleotide sequence of (d)" refers to a nucleotide sequence which, upon appropriate alignment, exhibits an identity of 85% or higher, preferably 90% or higher, more preferably 95% or higher to the nucleotide sequence of SEQ ID NO: 1.

The gene of the present invention can be readily obtained through a customary PCR technique by using a primer set prepared on the basis of the nucleotide sequence of SEQ ID NO: 1, and using, as a template, DNA of *Lactobacillus casei* YIT 9029.

Specifically, the gene of the present invention can be obtained through, for example, PCR by using a set of chemically synthesized oligonucleotides A and B (oligonucleotide A has a sequence including the N-terminal start codon of any of the aforementioned genes, and oligonucleotide B has a sequence complementary to a sequence including the stop codon of the gene), and using, as a template, DNA of *Lactobacillus casei* YIT 9029. For effective cloning of the thus-obtained gene fragment into, for example, a plasmid vector, a sequence for restriction enzyme cleavage may be added on the 5'-end side of the oligonucleotide primer. The primer which may be employed in the present invention is generally, for example, a nucleotide chemically synthesized on the basis of information on the nucleotide sequence of the gene of the present invention, but it may also be the gene of the present invention which has already been obtained or a fragment thereof. Such a nucleotide has a partial nucleotide sequence corresponding to, for example, SEQ ID NO: 1, and includes, for example, 10 to 50 consecutive nucleotides, and preferably 15 to 35 consecutive nucleotides.

When, for example, a DNA fragment having a length of 2,000 base pairs is prepared, PCR is carried out under the following conditions: 94° C. for 2 minutes, (95° C. for 10 seconds, 52° C. for 10 seconds, 72° C. for 2 minutes)×30 cycles, and 72° C. for 7 minutes.

The gene of the present invention may be artificially synthesized by means of a DNA synthesizer on the basis of the corresponding nucleotide sequence.

The gene of the present invention is a gene responsible for imparting hydrogen peroxide resistance. Therefore, when the gene of the present invention is introduced into a microorganism, or when the gene present in the microorganism is modified, hydrogen peroxide resistance can be imparted to the microorganism, or hydrogen peroxide resistance of the microorganism can be enhanced.

The gene of the present invention may be introduced into a microorganism which does not originally have the gene. Introduction of the gene may be carried out through, for example, the competence method using DNA uptake ability, the protoplast PEG method using a protoplast, or electroporation using high-voltage pulses. Particularly, electroporation is preferably employed. Integration of the gene into the chromosome of a microorganism may be carried out through homologous recombination or site-specific integration.

Modification of the gene of the present invention may be enhancement of expression of the gene.

Enhancement of expression of the gene of the present invention may be carried out through, for example, a method in which a recombinant plasmid carrying the gene is introduced into a microorganism of interest; a method in which the gene is integrated into another site of the chromosome through site-specific recombination, to thereby increase the number of copies of the gene in a microorganism; or a method in which the level of expression of the gene is increased by modifying a region for controlling expression of the gene or by modifying a regulatory gene. Particularly preferred is a method of increasing the number of copies of the gene. Specifically, the number of copies of the gene of interest may be increased in microbial cells through the following procedure: the gene (including the original promoter sequence and ribosome-binding site of the gene) or the polynucleotide (prepared by ligating only a polypeptide-encoding region of the gene to the downstream of a promoter and a ribosome-binding site which have been separated from another gene or chemically synthesized) is cloned into a plasmid having a plurality copies per microbial cell, and the plasmid is introduced into microbial cells through electroporation or a similar technique.

In the case of a microorganism which originally has the gene of the present invention, expression of the gene may be inhibited or suppressed, to thereby reduce hydrogen peroxide resistance of the microorganism.

For inhibition of expression of the gene of the present invention, the gene may be disrupted or deleted through the insertion-inactivation method in which a DNA fragment entirely different from a target gene is inserted into the gene, or the stepwise double crossover method in which the entirety or a portion of a target gene is deleted by stepwise homologous recombination. Particularly, the stepwise double crossover method is preferably employed.

Specifically, when the entirety or a portion of a target gene is deleted, two regions sandwiching the deletion region are separated from chromosomal DNA or separated following amplification by PCR, and the two DNA fragments are cloned into a plasmid vector such as pYSSE3 which can replicate in *Escherichia coli* but cannot in a microorganism of interest, so that the fragments are aligned in the same direction as the original direction. Subsequently, the resultant recombinant plasmid DNA is introduced, through electroporation or a similar technique, into a microorganism in which deletion is caused to occur. Through PCR or a similar technique, there is selected, from the resultant antibiotic-resistant clones, a clone in which the plasmid has been inserted into the chromosome through recombination in a region homologous to the above-cloned region upstream or downstream of the target deletion region. The thus-obtained clone is repeatedly subcultured in a medium containing no antibiotic, to thereby select clones which have lost antibiotic resistance through removal of the plasmid from the chromosome by recombination between flanking homologous regions and through disappearance of the plasmid in bacterial growth. Through PCR or a similar technique, there can be selected, from the thus-obtained clones, a clone in which the target gene region has been deleted.

Suppression of expression of the gene of the present invention may be carried out through the so-called RNA interference method in which a short RNA fragment complementary to the 5'-end region of mRNA of the gene is synthesized, or a method in which a regulatory gene or a region for controlling expression of the gene of the present invention is disrupted or deleted. Particularly, modification of a region for controlling expression of the gene of the present invention is preferred. Specifically, the amount of transcription of the gene of the present invention into mRNA can be increased or reduced by modifying the sequence of a promoter for controlling transcription of the gene.

No particular limitation is imposed on the microorganism into which the gene of the present invention is introduced or in which the gene is modified, and the microorganism may be, for example, a Gram-positive bacterium, a Gram-negative bacterium, or yeast. The microorganism employed is preferably a Gram-positive bacterium, particularly preferably, for example, a bacterium belonging to the genus *Lactobacillus* or *Bifidobacterium* which has been shown to be biologically safe. Among bacteria belonging to the genus *Lactobacillus*, bacteria of the *Lactobacillus casei* group, such as *Lactobacillus casei*, *Lactobacillus paracasei*, *Lactobacillus zeae*, and *Lactobacillus rhamnosus* are preferably employed, and *Lactobacillus casei* is particularly preferably employed.

Bacteria belonging to the genus *Bifidobacterium*, which are obligate anaerobes, are labile to oxygen, low pH, or high acidity, and often encounter difficulty in handling such as proliferation upon production, and survivability during storage. Since bacteria belonging to the genus *Bifidobacterium* exhibit physiological effects useful for humans, they have been applied to beverages, foods, or pharmaceutical products by, for example, producing a mutant strain exhibiting hydrogen peroxide resistance through improvement of breeding, or using an oxygen-impermeable container. However, the bacteria pose various problems, including difficult culturing, and a reduction in number of living cells during storage. Since bacteria belonging to the genus *Bifidobacterium* have been shown not to have the hydrogen peroxide resistance-imparting gene of the present invention, the bacteria can be preferably employed as a microorganism of interest in which the gene of the present invention is introduced or modified.

The thus-obtained microorganism into which the gene of the present invention has been introduced or in which the gene has been modified can be employed for producing a food, beverage, or pharmaceutical product effectively exhibiting various physiological effects that are intrinsic to the microorganism, since hydrogen peroxide resistance has been imparted to the microorganism or hydrogen peroxide resistance thereof has been enhanced.

When the microorganism of the present invention in which the gene of the present invention has been introduced or modified is incorporated into a food or beverage or in a pharmaceutical product, living cells, heated cells (dead cells), or lyophilized cells of the microorganism may be employed. Alternatively, a cultured product containing the microorganism may be employed, or processed cells of the microorganism may be employed. Preferably, living cells of the microorganism are employed.

When the microorganism of the present invention is employed in a pharmaceutical product, the microorganism may be mixed with a solid or liquid nontoxic carrier for pharmaceutical use, and the mixture may be administered in the form of a conventional pharmaceutical product. Examples of such a pharmaceutical product include solid products such as tablet, granules, powder, and capsule; liquid products such as solution, suspension, and emulsion; and lyophilized products. Such a pharmaceutical product may be prepared through a customary technique for pharmaceutical product production. Examples of the aforementioned nontoxic carrier for pharmaceutical use include glucose, lactose, sucrose, starch, mannitol, dextrin, fatty acid glyceride, polyethylene glycol, hydroxyethyl starch, ethylene glycol, polyoxyethylene sorbitan fatty acid ester, amino acid, gelatin, albumin, water, and saline. If necessary, the pharmaceutical product may appropriately contain a conventional additive such as a stabilizer, a humectant, an emulsifier, a binder, an isotonizing agent, or an excipient.

The microorganism of the present invention in which the gene of the present invention has been introduced or modified may also be incorporated into a food or beverage in addition to the aforementioned pharmaceutical product. When the microorganism is incorporated into a food or beverage, the microorganism may be employed as is, or mixed with various nutritional ingredients. The resultant food or beverage can be employed for producing a health food or food material effectively exhibiting various physiological effects that are intrinsic to the microorganism, since hydrogen peroxide resistance has been imparted to the microorganism or hydrogen peroxide resistance thereof has been enhanced. Specifically, when the microorganism obtained through the method of the present invention is incorporated into a food or beverage, the microorganism may be appropriately mixed with an additive which can be used in a food or beverage, and the mixture may be prepared, through conventional means, into a form suitable for edible use; for example, granules, particles, tablet, capsule, or paste. The microorganism may also be added to a variety of foods; for example, processed meat products such as ham and sausage, processed fish products such as kamaboko and chikuwa, bread, confectionary, butter, and powdered milk. Alternatively, the microorganism may be added to beverages such as water, fruit juice, milk, refreshing beverages, and tea beverages. As used herein, the term "food or beverage" encompasses animal feeds.

Examples of the food or beverage of the present invention include fermented foods and beverages produced by use of the microorganism of the present invention, such as fermented milk, lactic acid bacteria beverages, fermented soybean milk, fermented fruit juice, and fermented plant extract. Such a fermented food or beverage may be produced through a customary method. For example, a fermented milk product may be produced through the following procedure. Firstly, only the microorganism of the present invention is inoculated into a sterilized milk medium, or the microorganism and another microorganism are simultaneously inoculated into the medium, followed by culturing, and the cultured product is homogenized to thereby yield a fermented milk base. Subsequently, a separately prepared syrup is added to and mixed with the fermented milk base, and the mixture is homogenized by means of, for example, a homogenizer, followed by addition of a flavor to the resultant mixture, to thereby yield a final product. The thus-produced fermented milk product may be in any form, such as a plain-type product containing no syrup (sweetener), a soft-type product, a fruit-flavor-type product, a solid product, or a liquid product.

The microorganism produced through the method of the present invention exhibits high hydrogen peroxide resistance. Therefore, when the microorganism is incorporated into a food or beverage product, since the microorganism exhibits high survivability therein, a reduction in number of living cells or an increase in rate of cell death is suppressed during storage of the product. In addition, the specification of the product is readily maintained, and the product effectively exhibits general physiological effects such as regulation of intestinal functions of a microorganism including a bacterium belonging to the genus *Lactobacillus*. When hydrogen peroxide resistance is imparted, through the method of the present invention, to a bacterial strain belonging to the genus *Lactobacillus* or *Bifidobacterium* which originally has a specific physiological effect such as anticancer effect or *Helicobacter pylori* eradication effect, or when hydrogen peroxide resistance of the bacterial strain is enhanced through the method of the present invention, the bacterial strain can be applied to various foods and beverages, and the physiological effect of the bacterial strain can be enhanced by virtue of improvement of the survivability of the bacterial strain.

Hitherto, a container formed of an oxygen-impermeable packaging material such as glass and aluminum-coated paper has generally been used for storing a food or beverage product incorporating a bacterium belonging to the genus *Bifidobacterium* for the purpose of enhancing the survivability of the bacterium during storage of the product. However, the bacterium belonging to the genus *Bifidobacterium* produced through the method of the present invention, to which hydrogen peroxide resistance has been imparted or in which hydrogen peroxide resistance has been enhanced, realizes employment, as a container material, of a resin having high oxygen permeability (for example, polystyrene, polyethylene, or polyethylene terephthalate), since the bacterium exhibits high survivability and does not require strict anaerobic conditions. A container formed of such a resin is advantageous in that production cost can be reduced and the shape of the container can be changed freely, as compared with the case of a container formed of an oxygen-impermeable packaging material.

The gene of the present invention can also be employed for selecting, through screening, a microorganism exhibiting hydrogen peroxide resistance.

Specifically, a microorganism exhibiting hydrogen peroxide resistance can be selected through screening by determining the presence or absence of the gene of the present invention, and/or determining the level of expression of the gene.

In this case, for determination of the presence or absence of the gene and/or the level of expression of the gene, the presence or absence of a target gene in a microorganism, the number of copies of the gene, or the level of expression thereof is determined through southern hybridization, DNA microarray, or RT-PCR by use of a probe or primer which can detect the gene of the present invention or mRNA derived therefrom. A microorganism of interest can be selected on the basis of the presence or absence of the target gene or the level of expression of the gene.

The recombinant vector of the present invention containing any of the polynucleotides described in (d) to (f) or a portion (fragment) thereof can be obtained through a known technique such as in vitro ligation by use of any vector (for example, pHY400, pSA1, or pYSSE3) having such a gene marker that can determine introduction of the vector into *Escherichia coli* and a microorganism of interest.

A host microorganism containing the aforementioned recombinant vector can be obtained through a known method. Specifically, when the recombinant vector is introduced into a host microorganism, electroporation or a similar technique may be employed. When the recombinant vector is integrated into the chromosome of the microorganism, there may be employed a method in which a recombinant vector having a DNA region homologous to that of the microorganism is introduced through electroporation or a similar technique, and then the vector integrated into the chromosome by homologous recombination is determined through, for example, PCR.

The DNA array or DNA chip of the present invention containing any of the polynucleotides described in (d) to (f) or a portion (fragment) thereof can be prepared through a known technique such as photolithography. The DNA array or the DNA chip can be employed for selecting, through screening, a microorganism which expresses the gene of the present invention.

In order to effectively perform the aforementioned introduction of the gene of the present invention into a microorganism, modification of the gene, or screening of microorganisms, preferably, there is employed a recombinant vector containing the polynucleotide of the present invention or a portion thereof, a primer for PCR or RT-PCR containing a partial fragment of the polynucleotide of the present invention, a primer for PCR or RT-PCR which can amplify the polynucleotide of the present invention or a portion thereof, or a nucleic acid fragment for hybridization containing a polynucleotide which specifically hybridizes with the polynucleotide of the present invention or a portion of the polynucleotide.

The nucleic acid fragment such as a primer which may be employed in the present invention is generally, for example, a nucleotide chemically synthesized on the basis of information on the nucleotide sequence of the gene of the present invention. Preferably, such a nucleotide has a partial nucleotide sequence corresponding to the nucleotide sequence of SEQ ID NO: 1, and includes 10 to 50 consecutive nucleotides, and preferably 15 to 35 consecutive nucleotides.

Hereinafter, the present invention will be described in more detail by way of examples.

EXAMPLES

Example 1

Change in Expression Level of CDS2657 Gene Caused by Oxygen or Hydrogen Peroxide Stress The expression level of CDS2657 gene when exposed to oxygen or hydrogen peroxide was analyzed by using real time PCR.

(1) Addition of Oxidative Stress

For oxygen stress, culture was performed for seven hours in 100 ml anaerobic MRS medium. After the resultant culture liquid was divided into two groups, one was added to a 300 ml volume conical flask and the oxygen stress was applied by shaking for 30 minutes at 160 rpm using a shaking incubator manufactured by TAITEC Co., Ltd. For hydrogen peroxide stress, culture was performed for seven hours in 100 ml MRS medium in aerobic and static conditions. After the resultant culture liquid was divided into two groups, one was added with hydrogen peroxide at a concentration of 0.5 mM and the hydrogen peroxide stress was applied by additional culture for 30 minutes.

(2) RNA Preparation

The culture liquid cultured in an MRS medium (2 ml) was added to two volumes of RNAprotect Bacteria Reagent (QIAGEN) and stirred. By incubation for five minutes at room temperature, RNA was stabilized. Cells were collected by centrifugation for 10 minutes at 5000×g, and then suspended in TE buffer (200 µl) containing 15 mg/ml lysozyme. After adding 10 µl of 1 mg/ml N-acetyl muramidase SG (Seikagaku Corporation), the cells were incubated for 10 minutes at room temperature with occasional shaking by vortex. Buffer RLT of RNeasy Mini Kit (QIAGEN) (700 µl) was added for suspension, and the supernatant was collected by centrifugation for five minutes at 5000×g. After that, the purification was performed according to the protocols attached to RNeasy Mini Kit (QIAGEN) and RNAprotect Bacteria Reagent (QIAGEN). During the purification, DNase treatment was performed using RNase-Free DNase Set (QIAGEN) for DNA degradation.

Quality of the thus-prepared RNA was determined by using 2100 Bioanalyzer (Agilent).

(3) Quantitative Analysis of Gene Expression by Real Time PCR

For quantification of the expression level of the target gene (CDS2657 gene), real time PCR was performed. By using 1 µg total RNA as a template and PrimeScript 1st strand cDNA Synthesis Kit (Takara Bio Inc.), the reverse transcription reaction (30° C. for 10 minutes, 42° C. for 50 minutes, and 95° C. for five minutes) was performed to produce the cDNA. The diluted cDNA solution was used as a template. By adding SYBR Premix Ex Taq (Takara Bio Inc.) and primers and using 7500 Real Time PCR System (Applied Biosystems), the reaction including 95° C. 30 seconds followed by 40 cycles of 95° C. for five seconds and 60° C. for 34 seconds was performed. In addition, as to the gene expression level, 16S rRNA was taken as an internal standard and calibration among the samples was performed. The result was expressed as relative value of expression level of the stressed sample compared to expression level of the non-stressed sample. The primers used are listed in Table 1.

TABLE 1

| Gene name | Primer sequence (5'-3') | Sequence number |
|---|---|---|
| 16S rRNA | F CGTTCCCGGGCCTTGTAC | SEQ ID NO: 3 |
| 16S rRNA | R CGGCTTCGGGTGTTACAAA | SEQ ID NO: 4 |
| 2657 | F GCGCTGCCACTGGACAAC | SEQ ID NO: 5 |
| 2657 | R CAGACCACTGCCGAAATAATCC | SEQ ID NO: 6 |

(4) Result

Expression of CDS2657 gene was promoted by oxygen or hydrogen peroxide stress. The result was more significant in the case of hydrogen peroxide stress (FIG. 1).

Values of FIG. 1 indicate an average value obtained from three independent tests, and the error bar indicates standard deviation.

Example 2

Isolation of CDS2657 Gene-Disrupted Strain (1) Method for Gene Disruption

Employed were, as primers, an oligonucleotide 5'-cgcggatccggttcttgtgccattggaaa-3' (SEQ ID NO: 7), which had been designed by adding a sequence including a BamH I restriction site to the 5'-end of a sequence within the sequence of SEQ ID NO: 1, and an oligonucleotide 5'-aaactgcagtgtcatcacgcagagccaac-3' (SEQ ID NO: 8), which had been designed by adding a sequence including a Pst I restriction site to the 5'-end of a sequence selected from the sequence complementary to the sequence of SEQ ID NO: 1. By use of KOD Plus DNA polymerase (manufactured by TOYOBO, product code: KOD-201) and according to an instruction attached to the enzyme, PCR was carried out with DNA of *Lactobacillus casei* YIT 9029 as a template. The thus-amplified DNA fragment was a partial sequence of the CDS2657 gene lacking both the amino terminus and the carboxyl terminus. This product was mixed with an equiamount of Tris-EDTA (10 mM Tris (pH 8.0)-1 mM EDTA, hereinafter referred to as "TE") saturated phenol-chloroform-isoamyl alcohol (25:24:1). After thorough vortexing, the mixture was centrifuged at 15,000×g for five minutes, to thereby separate it into two layers. The upper layer (aqueous layer) was recovered, and 3 M sodium acetate solution (pH 5.2) (⅒ amount to the aqueous layer) and 99.5% ethanol (thrice amount to the aqueous layer) were added thereto. The resultant mixture was allowed to stand at −20° C. for 30 minutes or longer and then centrifuged at 4° C. and 15,000×g for 15 minutes. The supernatant was removed, and 70% ethanol was added to the precipitate for rinse. The thus-obtained mixture was centrifuged at 15,000×g for five minutes. Thereafter, ethanol was removed, and the precipitate was dried under vacuum.

The precipitate was digested with restriction enzymes BamH I and Pst I (manufactured by Takara Bio Inc.) at 37° C. for 20 hours in K buffer (manufactured by Takara Bio Inc.) reaction solution (100 µl). Subsequently, the aforementioned TE saturated phenol-chloroform-isoamyl alcohol treatment (mixing with solvent to recovery of aqueous layer) was carried out twice. An aqueous layer was recovered, and 3 M sodium acetate solution (pH 5.2) (1/10 amount to the aqueous layer) and 99.5% ethanol (thrice amount to the aqueous layer) were added thereto. The resultant mixture was allowed to stand at −20° C. for 30 minutes or longer, and then centrifuged at 4° C. and 15,000×g for 15 minutes. The supernatant was removed, and 70% ethanol was added to the precipitate for rinse. The thus-obtained mixture was centrifuged at 15,000×g for five minutes. Thereafter, ethanol was removed, and the precipitate was dried under vacuum.

As a plasmid vector, pYSSE3 (Yasuda et al. 2008. Appl. Environ. Microbiol. 74: 4746-4755) was used, which vector has a replication region for $E.$ $coli$ originating from plasmid pUC19 and has an erythromycin-resistant gene from plasmid pAMβ1, which functions both in $E.$ $coli$ and $Lactobacillus$. The pYSSE3 DNA was digested with restriction enzymes BamH I and Pst I (manufactured by Takara Bio Inc.) at 37° C. for 20 hours in K buffer (manufactured by Takara Bio Inc.) reaction solution (100 µl). Subsequently, a 10-fold concentrated CIP buffer (manufactured by TOYOBO) (20 µl) and water were added thereto so as to adjust the total volume to 200 µl, and calf intestine phosphatase (manufactured by TOYOBO) (3 µl) was added thereto, followed by incubation at 37° C. for two hours. Thereafter, the aforementioned TE saturated phenol-chloroform-isoamyl alcohol treatment and ethanol precipitation were carried out, and the precipitate was dried under vacuum.

The aforementioned DNA fragment consisting of an internal sequence of CDS2657 gene and the plasmid vector which had been digested with the restriction enzymes were mixed each in an amount of about 0.01 to about 0.1 µg, and an equivolume of Solution I of DNA ligation kit ver. 2.1 (manufactured by Takara Bio Inc.) was added to the mixture, followed by incubation at 16° C. for 30 minutes. Thereafter, the resultant product was placed on ice.

Next, the aforementioned reaction mixture (5 µl) was added to JM109 competent cells (manufactured by TOYOBO) (100 µl), which had been placed on ice after dissolution, and the mixture was incubated for 30 minutes on ice after mild mixing. Thereafter, the reaction mixture was subjected to heat shock (42° C. for 30 seconds), and then returned to ice. SOC medium (manufactured by TOYOBO) (1 mL) was added to the cell liquid, and culturing was carried out at 37° C. for one hour. The thus-cultured product was spread onto an LB agar medium (containing bacto-tryptone (10 g), bacto-yeast extract (5 g), sodium chloride (5 g), and agar (15 g in 1 L)) to which 500 µg/mL erythromycin (erythromycin for injection, manufactured by Dainabot) had been added, followed by incubation at 37° C.

The thus-formed erythromycin-resistant colonies were grown in an LB medium to which 500 µg/mL erythromycin had been added, and recombinant plasmid DNA was extracted by means of Wizard Plus SV Minipreps DNA Purification System (manufactured by Promega).

DNA transfer to $Lactobacillus$ $casei$ YIT 9029 was carried out through the following procedure. The relevant microorganism was grown in an MRS medium (manufactured by Difco), and a culture liquid in a logarithmic growth phase was centrifuged at 5,000×g and 4° C. for five minutes, whereby cells were collected. The cells were washed once with ice-cooled 20 mM HEPES (pH 7.0) and once with 10% glycerol, and the washed cells were suspended in 10% glycerol (initial Klett value of culture liquid×2 µl). The cell suspension (40 µl) and the recombinant plasmid DNA solution (2 µl) were mixed together, and the mixture was placed in a 2 mm-width cuvette for electroporation. Electroporation was carried out by means of Gene Pulser II (manufactured by Bio-Rad Laboratories, Inc.) at 1.5 kV voltages, 200Ω resistance, and 25 µF capacitance. An MRS medium (1 mL) was added to the thus-treated liquid, and the mixture was cultured at 37° C. for one hour. Subsequently, the thus-cultured product was spread onto an MRS agar medium to which 20 µg/mL erythromycin had been added, followed by incubation under anaerobic conditions (provided by means of AnaeroPack Kenki manufactured by Mitsubishi Gas Chemical Company, Inc.) at 37° C. for two or three days.

A portion of the thus-grown erythromycin-resistant colonies was collected and suspended in TE (50 µl), and then the suspension was treated at 94° C. for 2.5 minutes. A portion of the suspension was employed as a template for PCR. PCR analysis was carried out by using the following two primers: a primer selected from sequences located downstream of the CDS2657 gene of $Lactobacillus$ $casei$ YIT 9029 chromosome; and a primer selected from sequences which were included in the plasmid vector and in the vicinity of a cloned CDS2657 gene internal fragment. The PCR analysis revealed that the transferred plasmid was integrated into a region homologous to a CDS2657 gene fragment included in the recombinant plasmid in the $Lactobacillus$ $casei$ YIT 9029 chromosomal CDS2657 gene, whereby the CDS2657 gene was divided (disrupted). The thus-obtained clone was employed as $Lactobacillus$ $casei$ MS105 strain.

Example 3

Hydrogen Peroxide Resistance of CDS2657 Gene-Disrupted Strain (1) $Lactobacillus$ $casei$ MS105 strain obtained from Example 2 was cultured overnight in an MRS medium. After that, the cells were collected, washed twice with 50 mM potassium phosphate buffer (pH 6.8), and suspended in the same buffer so that the cells were 10-fold diluted. The suspension (3 ml) was poured in a small test tube with aluminum cap and added with hydrogen peroxide at a final concentration of 1 or 3 mM. After incubation for three hours at 37° C., cell number was counted so that the survival ratio compared to the cell number before hydrogen peroxide addition was obtained.

Figure 2:
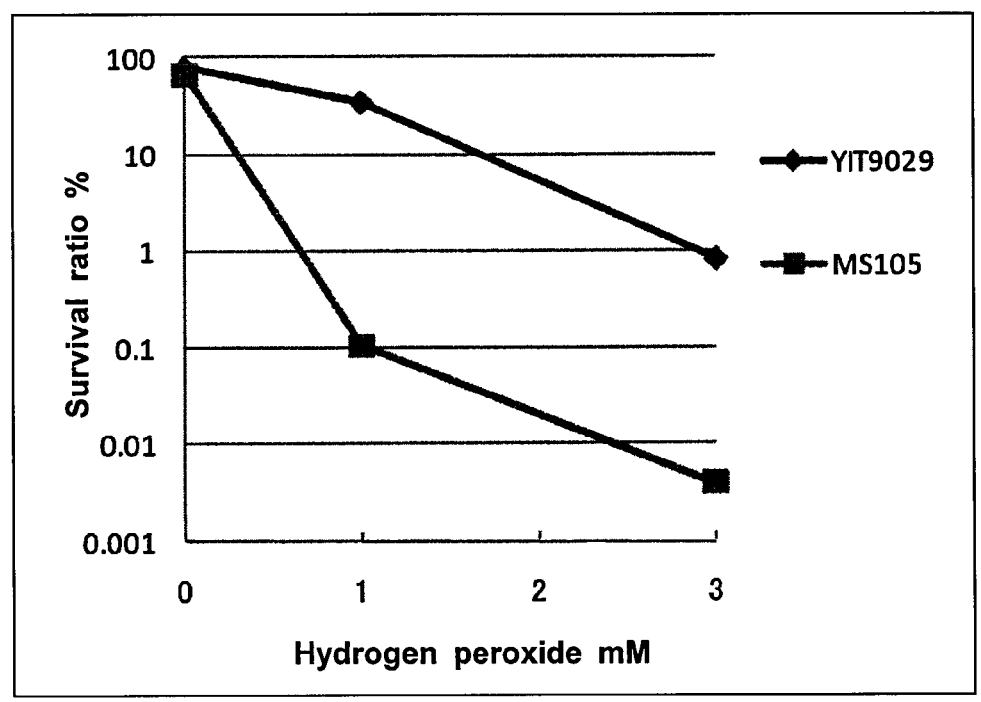
FIG. 2 is a graph illustrating the hydrogen peroxide resistance (survival ratio) of CDS2657 gene-disrupted strain.

(2) Result $Lactobacillus$ $casei$ MS105 strain exhibited the survival ratio which was lower by about two orders of magnitude than the wild type, exhibiting higher sensitivity to hydrogen peroxide (FIG. 2).

Example 4

Hydrogen Peroxide Elimination Activity of CDS2657 Gene-Disrupted Strain (1) $Lactobacillus$ $casei$ YIT 9029, $Lactobacillus$ $casei$ MS 105 and $Lactobacillus$ $casei$ MS 105 (NADH peroxidase disrupted strain) were used. Each strain was cultured in an MRS medium for seven hours and added with hydrogen peroxide at a final concentration of 0.5 mM, followed by culturing for one hour. From the resultant culture liquid, the cells were collected while the cell amount was adjusted such that OD660=1 for 1 ml. The cells were washed twice with 50 mM potassium phosphate buffer (pH 6.8) and suspended in the same buffer (0.1 ml). Then, the suspension (0.1 ml) and a hydrogen peroxide solution (0.9 ml), which had been prepared to have a final concentration of 100 µM with 90% volume, were mixed. After incubation for one hour at 37° C., remaining hydrogen peroxide concentration in the supernatant, which had been obtained by removing cells by centrifugation, was measured. The hydrogen peroxide concentration was measured by using BIOXYTECH $H_2O_2$-560 (Funakoshi Corporation).

Figure 3:
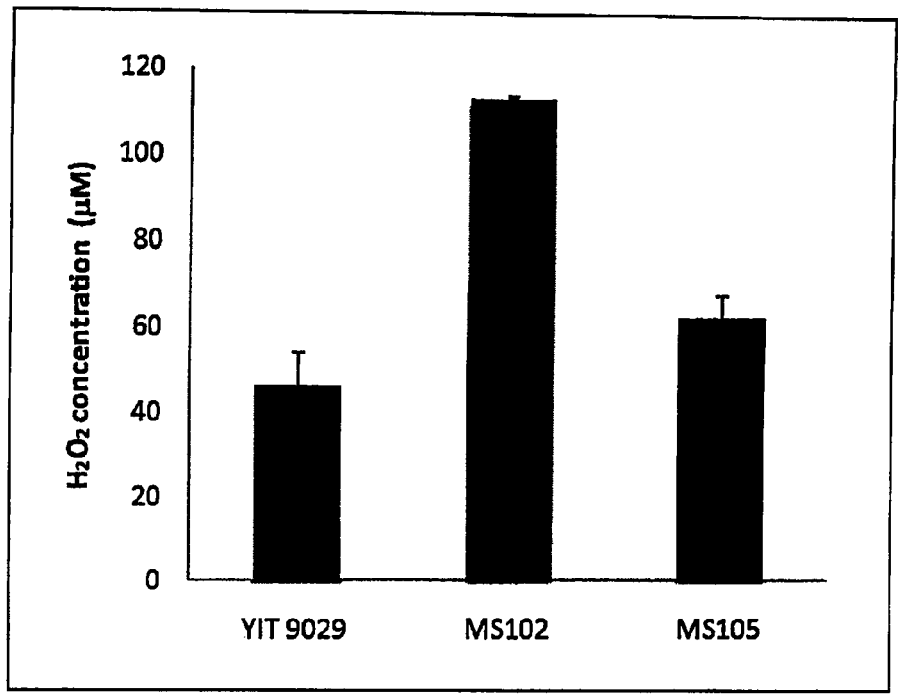
FIG. 3 is a graph illustrating the activity of eliminating hydrogen peroxide of CDS2657 gene-disrupted strain.

(2) Although *Lactobacillus casei* MS102 strain having disrupted NADH peroxidase was not able to eliminate hydrogen peroxide at all, *Lactobacillus casei* MS105 strain exhibited the hydrogen peroxide elimination activity which was equivalent to that of the wild type (FIG. 3). In the figure, concentration of remaining hydrogen peroxide after incubating the cells for one hour in 100 µM hydrogen peroxide solution was illustrated. The values indicate an average value obtained from three independent tests.

From the above, it was suggested that CDS2657 gene contributes to hydrogen peroxide resistance according to a mechanism that was distinct from hydrogen peroxide elimination.

Example 5

Cloning of CDS2657 Gene and Expression and Purification of CDS2657 Protein (1) Cloning of CDS2657 Gene into pET Vector By using a primer set (2657F:GGAATTCCATATG-CAAATCTCAATCAAACC (SEQ ID NO: 9) and 2657R: CGGAATTCTTAGCAAATTTTGCCGCCCA (SEQ ID NO: 10)) and using genomic DNA of *Lactobacillus casei* YIT 9029 as a template, PCR was performed with KOD-plus-DNA Polymerase (TOYOBO) to amplify a CDS2657 gene fragment. The obtained PCR product was subjected to electrophoresis and the DNA fragment of the desired size was excised from the gel and extracted and purified with QIAquick Gel Extraction Kit (QIAGEN). Further, the DNA fragment was digested with Nde I and EcoR I and purified using QIAquick PCR Purification Kit (QIAGEN). pET-28b (+) (Merck KGaA) was digested with Nde I and EcoR I and purified using QIAquick PCR Purification Kit (QIAGEN). The pET-28b (+) vector and the DNA fragment of CDS2657 were ligated to each other using DNA Ligation Kit ver. 2 (Takara Bio Inc.). The ligation reaction solution was introduced to *E. coli* JM109 (TOYOBO) for transformation. From the obtained transformants, plasmids were extracted by a common method, and then introduced to *E. coli* BL21 (DE3) competent cells (Merck KGaA) to give a transformant.

(2) Expression and Purification of Protein

Protein expression was performed according to the pET System Manual (Merck KGaA).

*E. coli* BL21 (DE3) transformant was cultured under shaking in 3 mL LB medium added with kanamycin (final concentration of 30 mg/ml). When $OD_{600}$ reached 0.6, the culture liquid was stored at 4° C. The culture liquid was inoculated to a fresh LB medium (200 ml) containing the antibiotic and cultured under shaking at 37° C. until $OD_{600}$ reached 0.6. IPTG was added thereto at a final concentration of 1 mM and culture was continued under shaking for three hours at 37° C. to induce the desired protein. The culture liquid was kept on ice for five minutes, and centrifuged for five minutes at 5000×g to collect the cells. The cells were washed with 20 mM cold Tris-HCl (pH 8.0×0.25 volume of the culture liquid), collected by centrifugation, and then stored at −80° C. until purification.

Preparation of cell lysate was performed using BugBuster Protein Extraction Reagent (Merck KGaA) according to the protocols attached thereto. Purification of protein was performed using Ni-NTA Fast Start Kit (QIAGEN) according to the protocols attached thereto. In order to confirm the purification degree, samples were taken at each step of the purification (5 ml for each) and then subjected to SDS-PAGE. SDS-PAGE was performed using NuPAGE 4-12% Bis-Tris Gel (Invitrogen) according to a common protocol.

Figure 4:
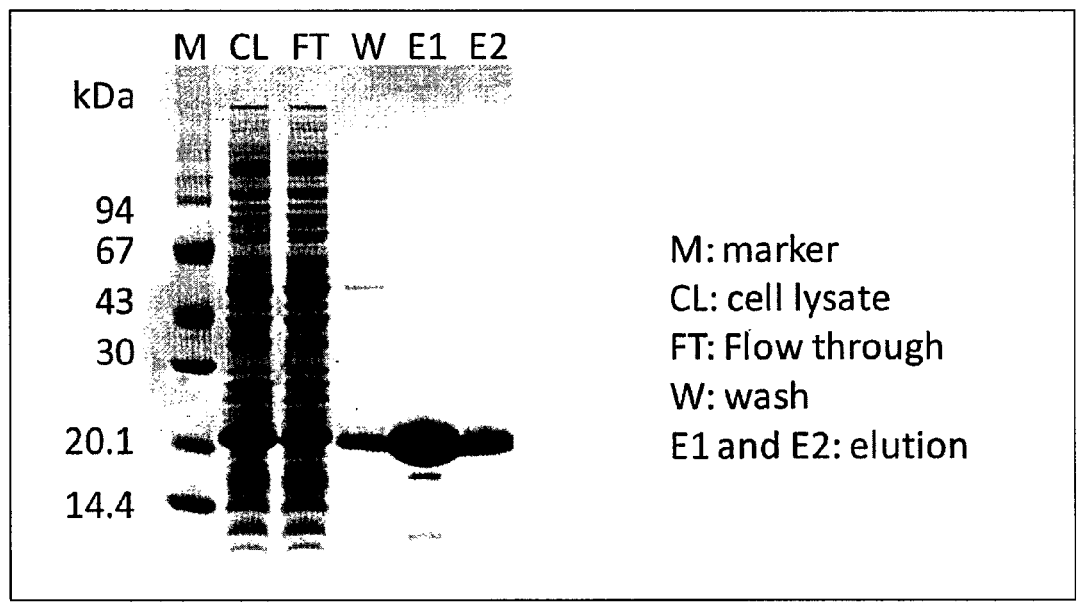
FIG. 4 illustrates SDS-PAGE pattern of CDS2657 protein. M: marker, CL: cell lysate, FT: flow through, W: wash, E1 & E2: elution.

As a result of performing the elution in two divided times, the first elution sample exhibited a weak minor band. However, as it had been purified almost to homogeneity, the one combined with the second elution liquid was taken as the purified protein and used for the following experiments (FIG. 4).

Example 6

Iron-Binding Ability of CDS2657 Protein (1) BSA (SIGMA) with No Iron-Binding Ability and Ferritin (Apoferritin from Equine Spleen, SIGMA) as an Iron-Binding Protein were Used as a Control.

<Preparation of Apoprotein>

Purified CDS2657 protein (200 µM) was incubated in the reaction solution containing 10 mM EDTA and 2 mM DTT for one hour at 37° C. The CDS2657 protein after the reaction was purified with a PD-10 column (GE Healthcare) equilibrated with water to remove EDTA and free iron ions.

<Iron-Binding Assay>

Apoprotein (50 µM) and Fe $(NH_4)_2$ $(SO_4)_2.6H_2O$ (10, 100, and 1000 µM) were incubated for five minutes at room temperature in the presence of 2 mM DTT (total volume was 1 ml). Meanwhile, since the reaction solution of the sample added with 1000 µM iron turned into reddish brown color, the sample was excluded from the measurement samples. The measurement samples were applied to a PD-10 column (GE Healthcare) equilibrated with water, and by removing free iron ions, protein fractions were purified. The protein fractions were filled up to 3 ml, and by using ICP spectrophotometer (Varian Technologies Japan Ltd.), iron concentration was measured.

(2) Result

CDS2657 protein exhibited an iron-binding ability, and when added with 100 µM iron, the CDS2657 protein binds to about two iron molecules per one molecule (Table 2).

TABLE 2

|  | Protein concentration (µM) | Iron concentration (µM) | Concentration of bound iron (mg/kg) | Iron molecules per protein (subunit) molecule |
|---|---|---|---|---|
| 2657 | 50 | 10 | 0.29 | 0.31 |
|  |  | 100 | 1.70 | 1.83 |
| BSA | 50 | 10 | <0.1 |  |
|  |  | 100 | <0.1 |  |
| Ferritin | 50 (subunit) | 10 | <0.1 |  |
|  |  | 100 | 0.27 | 0.29 |

The value represents an average value obtained from two independent tests.

Example 7

Suppression of Hydroxyl Radical Generation by CDS2657 Protein

Generation and detection of hydroxyl radicals were performed according to the methods reported by Halliwell (Halliwell, B., and J. M. Gutteridge, 1981. Formation of a thiobarbituric acid reactive substance from deoxyribose in the presence of iron salts. FEES Lett. 128: 347-352) and Yamamoto (Yamamoto, Y., L. B. Poole, R. R. Hantgan, and Y. Kamio. 2002, An iron-binding protein, Dpr, from *Streptococcus mutans* prevents iron-dependent hydroxyl radical formation in vitro. J. Bacteriol. 184: 2931-2939). Specifically, hydroxyl radicals were non-enzymatically generated using divalent iron, deoxyribose was degraded by the hydroxyl radicals, the resultant malondialdehyde-like substance was reacted with thiobarbituric acid to produce a red chromogen, and the fluorescence of the red chromogen was measured to determine the generation amount of hydroxyl radicals.

(1) Methods

To 0.3 ml basal reaction mixture (10 mM potassium phosphate buffer (pH 7.4), 63 mM NaCl, and 4 mM2-deoxyribose), a sample was added, $Fe(NH_4)_2(SO_4)_2.6H_2O$ was added thereto at a final concentration of 10 mM, and incubation was carried out for 15 minutes at 37° C. (total 2 ml). After adding 0.25 ml of 1% (w/v) thiobarbituric acid which had been dissolved by heating and 0.25 ml of 2.8% (w/v) trichloroacetic acid, the reaction solution was allowed to boil for 10 minutes and then rapidly cooled. The red chromogen generated was measured for fluorescence using fluorospectrophotometer (Shimadzu) with excitation at 532 nm and measurement at 553 nm. Then, the decrease from the fluorescence obtained from a case to which no sample was added was expressed as inhibitory rate on hydroxyl radical generation reaction (Table 3).

(2) Result

Deferoxamine (SIGMA) as an iron chelating agent suppressed the hydroxyl radical generation in a concentration dependent manner. CDS2657 also suppressed the hydroxyl radical generation in a concentration dependent manner. However, the ferrtin, an iron-binding protein, hardly suppressed the hydroxyl radical generation.

TABLE 3

| Sample | Concentration (µM) | Hydroxyl radical generation amount (arbitrary units) | Inhibition (%) |
|---|---|---|---|
| None |  | 310.2 ± 3.7 |  |
| 2657 | 0.1 | 329.2 ± 0.4 | <0 |
|  | 1 | 246.2 ± 16.2 | 20.6 ± 5.2 |
|  | 10 | 178.8 ± 2.2 | 42.4 ± 0.7 |
| BSA | 1 | 326.1 ± 4.9 | <0 |
|  | 10 | 863.9 ± 22.2 | <0 |
| Ferritin | 0.1 | 321.5 ± 1.6 | <0 |
|  | 1 | 306.3 ± 11.1 | 1.3 ± 3.6 |
|  | 10 | 387.8 ± 9.2 | <0 |
| Deferoxamine | 1 | 309.4 ± 7.4 | 0.3 ± 2.4 |
|  | 10 | 237.5 ± 4.4 | 23.4 ± 1.4 |
|  | 100 | 58.3 ± 2.6 | 81.2 ± 0.8 |

Measurement was performed in three series, and the value was expressed as average value±standard deviation.

From the above, it was suggested that CDS2657 protein involves in the hydrogen peroxide resistance by removing intracellular iron and suppressing generation of hydroxyl radicals.

Example 8

Effects of CDS2657-Overexpressing Strain on Hydrogen Peroxide (1) Preparation of CDS2657-Overexpressing Strain The CDS2657-overexpressing strain was prepared by introducing into *Lactobacillus casei* YIT 9029 a plasmid having CDS2657 gene introduced to pLP10 vector, in which a synthetic promoter sequence functioning in *Lactobacillus casei* YIT 9029 was placed upstream of multi-cloning site (Yasuda et al. 2008. Appl. Environ. Microbiol. 74: 4746-4755, Kiwaki et al. 2002. Biosci. Microflora 20: 121-129).

Primers were designed with a BamH I restriction site and a Pst I restriction site to amplify a sequence from the SD sequence upstream of CDS2657 gene to the terminal codon (2657outF: cgcggatccaatagagaggatggttcgga (SEQ ID NO: 11) and 2657outR:aaactgcagttagcaaattttgccgcc (SEQ ID NO: 12)). By using the primer set and genomic DNA of *Lactobacillus casei* YIT 9029 as a template, PCR was performed using KOD-plus-DNA Polymerase (TOYOBO) to amplify a CDS2657 gene fragment. The obtained PCR product was subjected to electrophoresis and the DNA fragment of the desired size was excised from the gel and extracted and purified with QIAquick Gel Extraction Kit (QIAGEN). Further, the DNA fragment was digested with BamH I and Pst I and purified using QIAquick PCR Purification Kit (QIAGEN). pLP10 was digested with BamH I and Pst I and purified using QIAquick PCR Purification Kit (QIAGEN). The pLP10 vector and the DNA fragment of CDS2657 were ligated to each other using DNA Ligation Kit ver. 2.1 (Takara Bio Inc.). The ligation reaction solution was introduced to *E. coli* JM109 competent cells (TOYOBO) for transformation.

The thus-obtained transformants were grown in an LB medium to which 500 µg/mL erythromycin had been added, and recombinant plasmid DNA was extracted by means of Wizard Plus SV Minipreps DNA Purification System (manufactured by Promega K.K).

DNA, transfer to *Lactobacillus casei* YIT 9029 was carried out through the following procedure. The relevant microorganism was grown in an MRS medium (manufactured by Difco), and a culture liquid in a logarithmic growth phase was centrifuged at 5,000×g and 4° C. for five minutes, whereby cells were collected. The cells were washed once with ice-cooled 20 mM HEPES (pH 7.0) and once with 10% glycerol, and the washed cells were suspended in 10% glycerol (initial Klett value of culture liquid×2 µl). The cell suspension (40 µl) and the recombinant plasmid DNA solution (2 µl) were mixed together, and the mixture was placed in a 2 mm-width cuvette for electroporation. Electroporation was carried out by means of Gene Pulser II (manufactured by Bio-Rad Laboratories, Inc.) at 1.5 kV voltages, 200Ω resistance, and 25 µF capacitance. An MRS medium (1 mL) was added to the thus-treated liquid, and the mixture was cultured at 37° C. for one hour. Subsequently, the thus-cultured product was spread onto an MRS agar medium to which 20 µg/mL erythromycin had been added, followed by incubation at 37° C. for two or three days.

A portion of the thus-grown erythromycin-resistant colonies was collected and suspended in TE (50 µl), and then the suspension was treated at 94° C. for 2.5 minutes. A portion of the suspension was employed as a template for PCR. PCR analysis was carried out using the primers which have sequences located upstream or downstream of multi-cloning site of pLP10. The PCR analysis revealed that the plasmid having CDS2657 inserted to pLP10 was introduced to *Lactobacillus casei* YIT 9029. The thus-obtained clone was employed as *Lactobacillus casei* MS106 (deposited at National Institute of Advanced Industrial Science and Technology (zip code: 305-8566, Tsukuba Central 6, 1-1-1 Higashi, Tsukuba, Ibaraki, Japan), as FERM BP-11476 on Feb. 25, 2011).

(2) Effect of Hydrogen Peroxide Addition on Growth

*Lactobacillus casei* YIT 9029, *Lactobacillus casei* MS105 strain having disrupted CDS2657, *Lactobacillus casei* MS101 having pLP10 vector introduced to *Lactobacillus casei* YIT 9029, and *Lactobacillus casei* MS106 overexpressing CDS2657 were used.

Each strain was inoculated to an MRS medium and cultured at 37° C. under aerobic and static conditions. Seven hours after culture, hydrogen peroxide was added thereto at a final concentration of 0, 1.5, or 3 mM, and culture was continued under aerobic and static conditions. Growth from seven to 24 hours was expressed as an increase amount of turbidity as measured by Klett-Summerson colorimeter.

(3) Result

Figure 5:
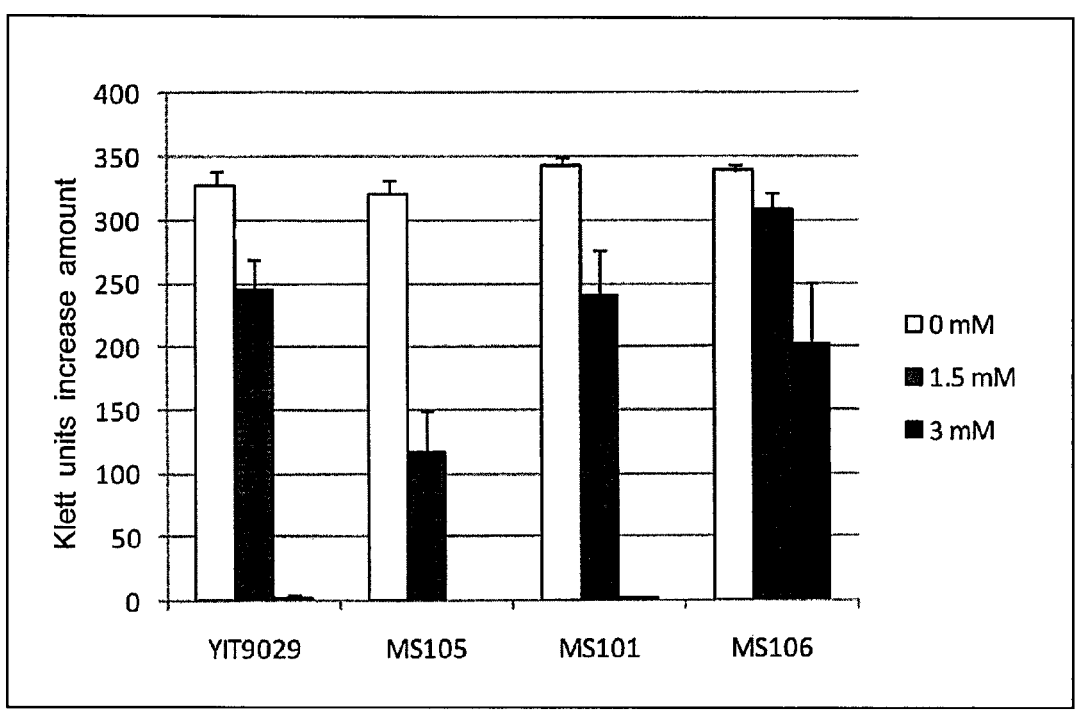
FIG. 5 is a graph illustrating the effect of hydrogen peroxide on growth of CDS2657 gene-overexpressing strain.

In the strain overexpressing CDS2657 (i.e., MS106), turbidity increase after 24 hours which was higher than the other strains tested was observed even when hydrogen peroxide was added at a concentration of 1.5 mM or 3 mM. The difference was significant when hydrogen peroxide was added at a concentration of 3 mM (FIG. 5).

The invention claimed is:

1. A method for imparting hydrogen peroxide resistance to or enhancing hydrogen peroxide resistance in a microorganism, the method comprising introducing a hydrogen peroxide resistance-imparting gene into a microorganism, or modifying the gene present in the microorganism,
    wherein the hydrogen peroxide resistance-imparting gene encodes a protein selected from the group consisting of the following proteins (a) to (c):
    (a) a protein having the amino acid sequence of SEQ ID NO: 2;
    (b) a protein which has an amino acid sequence equivalent to the amino acid sequence of (a), except that one to several amino acid residues are deleted, substituted, or added, and which exhibits hydrogen peroxide resistance-imparting activity; and
    (c) a protein which has an amino acid sequence having an identity of 85% or higher to the amino acid sequence of (a), and which exhibits hydrogen peroxide resistance-imparting activity.

2. The method according to claim 1, wherein the hydrogen peroxide resistance-imparting gene has a polynucleotide selected from the group consisting of the following polynucleotides (d) to (f):
    (d) a polynucleotide having the nucleotide sequence of SEQ ID NO: 1;
    (e) a polynucleotide which hybridizes, under stringent conditions, with a polynucleotide having a nucleotide sequence complementary to the nucleotide sequence of (d), and which encodes a protein exhibiting hydrogen peroxide resistance-imparting activity; and
    (f) a polynucleotide which has a nucleotide sequence having an identity of 85% or higher to the nucleotide sequence of (d), and which encodes a protein exhibiting hydrogen peroxide resistance-imparting activity.

3. The method according to claim 1, comprising modifying the gene present in the microorganism such that expression of the gene is enhanced.

4. A food or beverage, comprising a microorganism into which a hydrogen peroxide resistance-imparting gene has been introduced or in which the gene has been modified,
    wherein the hydrogen peroxide resistance-imparting gene encodes a protein selected from the group consisting of the following proteins (a) to (c):
    (a) a protein having the amino acid sequence of SEQ ID NO: 2;
    (b) a protein which has an amino acid sequence equivalent to the amino acid sequence of (a), except that one to several amino acid residues are deleted, substituted, or added, and which exhibits hydrogen peroxide resistance-imparting activity; and
    (c) a protein which has an amino acid sequence having an identity of 85% or higher to the amino acid sequence of (a), and which exhibits hydrogen peroxide resistance-imparting activity.

5. A pharmaceutical product, comprising a microorganism into which a hydrogen peroxide resistance-imparting gene has been introduced or in which the gene has been modified,
    wherein the hydrogen peroxide resistance-imparting gene encodes a protein selected from the group consisting of the following proteins (a) to (c):
    (a) a protein having the amino acid sequence of SEQ ID NO: 2;
    (b) a protein which has an amino acid sequence equivalent to the amino acid sequence of (a), except that one to several amino acid residues are deleted, substituted, or added, and which exhibits hydrogen peroxide resistance-imparting activity; and
    (c) a protein which has an amino acid sequence having an identity of 85% or higher to the amino acid sequence of (a), and which exhibits hydrogen peroxide resistance-imparting activity.

6. The method according to claim 2, comprising modifying the gene present in the microorganism such that expression of the gene is enhanced.

* * * * *

SEQUENCE LISTING

```
<160> NUMBER OF SEQ ID NOS: 12

<210> SEQ ID NO 1
<211> LENGTH: 405
<212> TYPE: DNA
<213> ORGANISM: Lactobacillus casei
<220> FEATURE:
<221> NAME/KEY: CDS
<222> LOCATION: (1)..(405)

<400> SEQUENCE: 1 atg caa atc tca atc aaa cca gca gca gtc act tac ttg aag gat cat        48
Met Gln Ile Ser Ile Lys Pro Ala Ala Val Thr Tyr Leu Lys Asp His
1               5                   10                  15 gtc aat cag gat caa cgg tta ttc ttg gca ctg gat gac ggc tca agc        96
Val Asn Gln Asp Gln Arg Leu Phe Leu Ala Leu Asp Asp Gly Ser Ser
                20                  25                  30 aaa tat tcc aaa ctt ggc ggt tct tgt gcc att gga aat aaa tat cag       144
Lys Tyr Ser Lys Leu Gly Gly Ser Cys Ala Ile Gly Asn Lys Tyr Gln
            35                  40                  45 tta gtg gtt gcc gat gag gat gat caa gat tat gcg ctg cca ctg gac       192
Leu Val Val Ala Asp Glu Asp Asp Gln Asp Tyr Ala Leu Pro Leu Asp
        50                  55                  60 aac gaa gct ggt ttc aaa ctg aca acg ggt gac cca gaa acg gat tat       240
Asn Glu Ala Gly Phe Lys Leu Thr Thr Gly Asp Pro Glu Thr Asp Tyr
65                  70                  75                  80 ttc ggc agt ggt ctg aca ctt gat ttc aaa aac gca tcg ttg gct ctg       288
Phe Gly Ser Gly Leu Thr Leu Asp Phe Lys Asn Ala Ser Leu Ala Leu
                85                  90                  95 cgt gat gac agc ggc att ctt gat ggg gct gtg acc ttg aat aag gac       336
Arg Asp Asp Ser Gly Ile Leu Asp Gly Ala Val Thr Leu Asn Lys Asp
                100                 105                 110 gcc gcc tta cca caa aat gat gca caa cgt cgg gat gac atg aca aaa       384
Ala Ala Leu Pro Gln Asn Asp Ala Gln Arg Arg Asp Asp Met Thr Lys
            115                 120                 125 ctg ggc ggc aaa att tgc taa                                            405
Leu Gly Gly Lys Ile Cys
        130

<210> SEQ ID NO 2
<211> LENGTH: 134
<212> TYPE: PRT
<213> ORGANISM: Lactobacillus casei

<400> SEQUENCE: 2

Met Gln Ile Ser Ile Lys Pro Ala Ala Val Thr Tyr Leu Lys Asp His
```

```
  1               5                  10                  15
Val Asn Gln Asp Gln Arg Leu Phe Leu Ala Leu Asp Asp Gly Ser Ser
               20                  25                  30

Lys Tyr Ser Lys Leu Gly Gly Ser Cys Ala Ile Gly Asn Lys Tyr Gln
           35                  40                  45

Leu Val Val Ala Asp Glu Asp Gln Asp Tyr Ala Leu Pro Leu Asp
       50                  55                  60

Asn Glu Ala Gly Phe Lys Leu Thr Thr Gly Asp Pro Glu Thr Asp Tyr
 65                  70                  75                  80

Phe Gly Ser Gly Leu Thr Leu Asp Phe Lys Asn Ala Ser Leu Ala Leu
               85                  90                  95

Arg Asp Asp Ser Gly Ile Leu Asp Gly Ala Val Thr Leu Asn Lys Asp
               100                 105                 110

Ala Ala Leu Pro Gln Asn Asp Ala Gln Arg Arg Asp Asp Met Thr Lys
           115                 120                 125

Leu Gly Gly Lys Ile Cys
       130
```

```
<210> SEQ ID NO 3
<211> LENGTH: 18
<212> TYPE: DNA
<213> ORGANISM: Artificial
<220> FEATURE:
<223> OTHER INFORMATION: primer sequence specific to 16SrRNA

<400> SEQUENCE: 3
cgttcccggg ccttgtac                                              18

<210> SEQ ID NO 4
<211> LENGTH: 19
<212> TYPE: DNA
<213> ORGANISM: Artificial
<220> FEATURE:
<223> OTHER INFORMATION: primer sequence specific to 16SrRNA

<400> SEQUENCE: 4
cggcttcggg tgttacaaa                                             19

<210> SEQ ID NO 5
<211> LENGTH: 18
<212> TYPE: DNA
<213> ORGANISM: Artificial
<220> FEATURE:
<223> OTHER INFORMATION: primer sequence specific to CDS2657 gene

<400> SEQUENCE: 5
gcgctgccac tggacaac                                              18

<210> SEQ ID NO 6
<211> LENGTH: 22
<212> TYPE: DNA
<213> ORGANISM: Artificial
<220> FEATURE:
<223> OTHER INFORMATION: primer sequence specific to CDS2657 gene

<400> SEQUENCE: 6
cagaccactg ccgaaataat cc                                         22

<210> SEQ ID NO 7
<211> LENGTH: 29
<212> TYPE: DNA
<213> ORGANISM: Artificial
```

```
<220> FEATURE:
<223> OTHER INFORMATION: primer sequence specific to CDS2657 gene

<400> SEQUENCE: 7
cgcggatccg gttcttgtgc cattggaaa                                    29

<210> SEQ ID NO 8
<211> LENGTH: 29
<212> TYPE: DNA
<213> ORGANISM: Artificial
<220> FEATURE:
<223> OTHER INFORMATION: primer sequence specific to CDS2657 gene

<400> SEQUENCE: 8
aaactgcagt gtcatcacgc agagccaac                                    29

<210> SEQ ID NO 9
<211> LENGTH: 30
<212> TYPE: DNA
<213> ORGANISM: Artificial
<220> FEATURE:
<223> OTHER INFORMATION: primer sequence specific to CDS2657 gene

<400> SEQUENCE: 9
ggaattccat atgcaaatct caatcaaacc                                   30

<210> SEQ ID NO 10
<211> LENGTH: 28
<212> TYPE: DNA
<213> ORGANISM: Artificial
<220> FEATURE:
<223> OTHER INFORMATION: primer sequence specific to CDS2657 gene

<400> SEQUENCE: 10
cggaattctt agcaaatttt gccgccca                                     28

<210> SEQ ID NO 11
<211> LENGTH: 29
<212> TYPE: DNA
<213> ORGANISM: Artificial
<220> FEATURE:
<223> OTHER INFORMATION: primer sequence specific to CDS2657 gene

<400> SEQUENCE: 11
cgcggatcca atagagagga tggttcgga                                    29

<210> SEQ ID NO 12
<211> LENGTH: 27
<212> TYPE: DNA
<213> ORGANISM: Artificial
<220> FEATURE:
<223> OTHER INFORMATION: primer sequence specific to CDS2657 gene

<400> SEQUENCE: 12
aaactgcagt tagcaaattt tgccgcc                                      27
```